United States Patent [19]

Faust

[11] 4,029,105

[45] June 14, 1977

[54] TRACHEOSTOMY AND ENDOTRACHEAL UNITS

[75] Inventor: Robert C. Faust, Greenfield, Wis.

[73] Assignee: Will Ross, Inc., Milwaukee, Wis.

[22] Filed: Nov. 26, 1975

[21] Appl. No.: 635,684

[52] U.S. Cl. .................................. 128/351; 16/109; 29/282; 138/174; 403/226

[51] Int. Cl.² ........................................ A61M 25/00

[58] Field of Search ........... 128/348, 349 R, 349 B, 128/349 BV, 350 R, 350 V, 351; 16/108, 109; 29/280, 282; 138/109, 138, 174; 285/423; 403/226, 228, 267, 269

[56] References Cited

UNITED STATES PATENTS

| | | | |
|---|---|---|---|
| 1,939,872 | 12/1933 | Bedur | 138/138 X |
| 2,765,792 | 10/1956 | Nichols | 128/351 |
| 3,156,489 | 11/1964 | Deringer | 138/174 X |
| 3,334,631 | 8/1967 | Stebleton | 128/351 |
| 3,540,759 | 11/1970 | Schneider | 285/423 X |
| 3,614,137 | 10/1971 | Jacobsen | 138/174 X |
| 3,631,848 | 1/1972 | Muller | 128/348 X |
| 3,693,624 | 9/1972 | Shiley et al. | 128/351 |

Primary Examiner—Edgar S. Burr
Assistant Examiner—Paul T. Sewell
Attorney, Agent, or Firm—John A. Dhuey

[57] ABSTRACT

Tracheostomy tube units are provided with a nonresilient annular ring within the tubing connector wall intermediate a tubing connector ferrule and the distal end of the tubing connector, thereby preventing inadvertent and undesired removal of the ferrule during connection and disconnection of accessory tubing.

4 Claims, 4 Drawing Figures

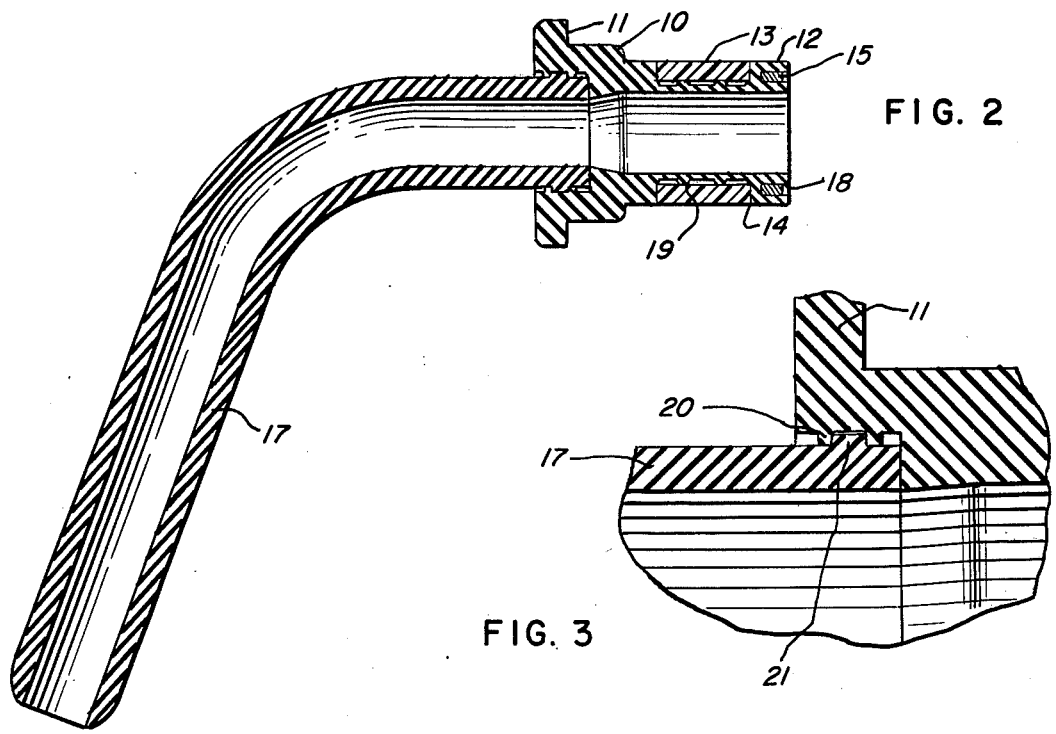
FIG. 2
FIG. 3
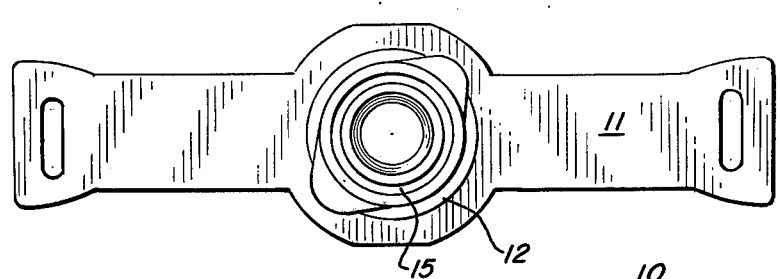
FIG. 4
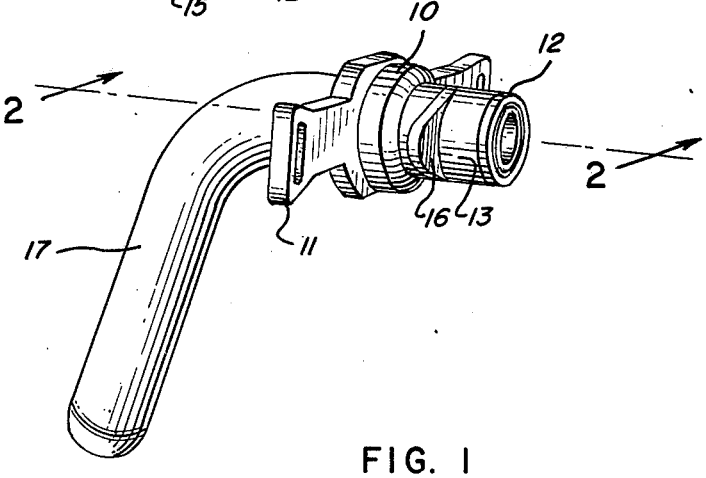
FIG. 1

TRACHEOSTOMY AND ENDOTRACHEAL UNITS

The present invention is concerned with improvements in resilient tubes, commonly used in respiratory care, which require connection and disconnection to other tubes or connectors which may or may not be resilient themselves.

Prior art tracheostomy strap connectors generally provide a strap integrally joined with a tubing connector. Since such strap connectors most often are manufactured from resilient material, e.g. silicone rubber, attachment of accessory tubing thereto, as for example from an anesthetic delivery device or a respirator, presents problems both in making and retaining a tight connection. In order to overcome that difficulty, it is common practice to place a non-resilient ferrule around the distal end of the tubing connector. Accessory tubing then is connected by forcing the end of the accessory tubing over the ferrule to provide a friction fit. Retention of the ferrule on the tubing connector often is accomplished with the aid of a continuous circumferential groove formed on the outer surface of the tubing connector.

In respiratory care operations it frequently is necessary to remove accessory tubing to permit various medical operations, such as suctioning, and then reattach such tubing for continued respiratory care. The retention groove, however, is not adequate to prevent frequent inadvertent removal of the ferrule during detachment of the accessory tubing because of the natural resiliency of the tube connector. If the ferrule is removed, it must be replaced on the tube connector so that subsequent accessory tubing connection can again be made. The undesirable and possibly life-threatening delay caused by the noted deficiency in prior art devices is eliminated by virtue of the invention hereinafter described.

The invention is best illustrated with reference to the following drawings wherein:

FIG. 1 is a perspective view of one embodiment of the invention;

FIG. 2 is a section view of the embodiment shown in FIG. 1;

FIG. 3 is an enlarged view of the connection between the tracheostomy tube connector and the tracheostomy tube; and FIG. 4 is an end view of the tracheostomy tube connector.

With reference to FIGS. 1–4, the tracheostomy tube unit comprises a strap connector 10 having a strap 11 integrally joined to a tubing connector 12. Tubing connector 12 has a circumferential groove 14 formed in the outer surface thereof to accept a ferrule 13. Ferrule 13 is positioned in groove 14 and adapted to receive accessory tubing connections from respirators, anesthetic devices and the like. In the distal end of tubing connector 12 is a groove 18, preferably circular. As shown in FIG. 2, the depth of groove 14 and outer diameter of ferrule 13 preferably are dimensioned so that the outer surface of ferrule 13 is generally flush with outer surface of tubular connector 12 and the wall thickness of ferrule 13 is approximately equal to the depth of groove 14.

It has been discovered that placement of a nonresilient annular ring 15 (as best seen in FIGS. 1, 2 and 4) within the distal end of tubing connector 12 and outwardly spaced from ferrule 13 prevents inadvertent detachment of ferrule 13 during removal of accessory tubing from tubing connector 12. The non-resilient annular ring can be made from any rigid material such as plastic or metal (e.g. stainless steel, polypropylene, and the like) and is placed intermediate ferrule 13 and the distal end of tubing connector 12, within continuous groove 18 formed in the distal end of tubing connector 12. Ring 15 is sealed within groove 18 by conventional methods. Since ring 15 is non-resilient, forces naturally associated with removal of tubing from ferrule 13 are no longer able to force ferrule 13 from the end of tube 12. As shown in FIG. 2, it is preferable to construct ring 15 with an outside diameter greater than the inside diameter of ferrule 13.

A preferred method of assembling the device described herein comprises placing an appropriately sized ferrule 13 within groove 14 on tubing connector unit 12, which has been molded with grooves 14 and 18 formed therein. This is easily accomplished in view of the material resiliency of tube 12 in the absence of ring 15 by forcing the end of tube 12 through ferrule 13. Then, ring 15 is placed in groove 18 and retained in place with any high strength adhesive. High strength Silicone adhesives are satisfactory for such a purpose. Preferably the top portion is sealed further with self-leveling silicone adhesive to form a smooth surface on the distal end of tube 12.

The completed tracheostomy strap connector then can be attached to a conventional tracheostomy tube 17, as shown most clearly in FIGS. 1 and 2. It has been found advantageous to construct ferrule 13 with finger tabs 16 on the outer surface thereof. Tabs 16 facilitate gripping of the connector unit when accessory tubing is being attached or detached.

In a particularly preferred embodiment of this invention, the proximal end of strap connector 10 is provided on its inner surface with circumferential rib extensions 20. Those extensions aid in gripping the tracheostomy tube which is provided with circumferential rib 21 on its outer surface. Rib 21 fits between ribs 20 to firmly anchor tracheostomy tube 17 to strap connector 10.

Groove 14, adaptable to receive ferrule 13, also is provided with circumferential rib extensions 19. Ribs 19 permit ferrule 13 to rotate on tubing connector 12 with relative ease. Since a certain amount of clearance between ferrule 13 and groove 14 preferably is provided, ribs 19 also aid in the retention of ferrule 13 on tubing connector 12 when it has been positioned properly.

Tubing connector 12 remains as described hereinbefore, having circumferential groove 18 in its distal end wherein is retained annular member 15. The bore of tubing connector 12 generally is sized to approximate the bore size of the tracheostomy tube.

It also is apparent that the instant invention can be used in other than tracheostomy tube connectors. Accordingly, resilient endotracheal tubes of conventional design may have an annular ring inserted in the distal end thereof to facilitate accessory tube attachment and prevent inadvertent removal of a tubing attachment ferrule when one is employed. Various other modifications will be apparent to those skilled in the art without departing from the intent and scope of this invention.

What is claimed is:

1. In a tracheostomy tube strap having a portion adapted for retention on a patient and an integral, resilient tubular connector having a ferrule on the outer surface thereof for operable engagement with respiratory apparatus, the improvement which comprises a non-resilient annular member contained within the wall of the tubular connector at a position intermediate the ferrule and the distal end of the connector, whereby said annular member prevents removal of the ferrule.

2. A tracheostomy tube connector unit comprising a substantially flat strap portion adapted for retention on a patient and having an opening therein, a hollow, resilient, tubular connector joined to said strap over said opening, said tubular connector having a continuous circumferential first groove on the outer surface thereof and a continuous second groove in the distal end thereof, a ferrule positioned within said first groove for operable engagement with respiratory apparatus and a non-resilient annular ring effectively preventing removal of said ferrule during respiratory care operations.

3. A tracheostomy tube connector unit as in claim 2 wherein the depth of said first groove is substantially equal to the wall thickness of said ferrule.

4. A tracheostomy tube connector unit as in claim 3 wherein the outside diameter of said annular ring is greater than the inside diameter of said ferrule.

* * * * *